United States Patent [19]

Seibyl et al.

[11] Patent Number: 5,447,948
[45] Date of Patent: Sep. 5, 1995

[54] DOPAMINE AND NORADRENERGIC REUPTAKE INHIBITORS IN TREATMENT OF SCHIZOPHRENIA

[75] Inventors: John P. Seibyl, Branford; John H. Krystal, New Haven; Dennis S. Charney, Hamden, all of Conn.

[73] Assignee: Yale University, New Haven, Conn.

[21] Appl. No.: 880,127

[22] Filed: May 7, 1992

[51] Int. Cl.⁶ .............. A61K 31/415; A61K 31/445
[52] U.S. Cl. .................................... 514/393; 514/327
[58] Field of Search ............................ 514/327, 393

[56] References Cited

U.S. PATENT DOCUMENTS 5,177,081 1/1993 Kaminski .................... 514/471
5,190,965 3/1993 Ruigt et al. ................. 514/401

OTHER PUBLICATIONS

Delwaide et al., "Mazindol in the Treatment of Parkinson's Disease," Arch. Neurol., vol. 40, pp. 788–790 (Dec. 1983).
Krumholz et al., "Clinical Evaluation of Mazindol in Chronic Schizophrenics," Current Therapeutic Research, vol. 12, No. 9, pp. 609–610 (Sep. 1970).
Joyce et al., *Biosis,* AN 89:162887, BA87:84988, 1988.
Chinaglia et al., *Medline,* AN 93063820, 1992.
Hirai et al., *Medline,* AN 89126127, 1988.

Primary Examiner—Raymond Henley, III
Assistant Examiner—William R. A. Jarvis
Attorney, Agent, or Firm—Millen, White, Zelano, & Branigan

[57] ABSTRACT

Mazindol and other dopamine and/or noradrenergic reuptake inhibitors are effective to treat negative symptoms in schizophrenia.

13 Claims, No Drawings

DOPAMINE AND NORADRENERGIC REUPTAKE INHIBITORS IN TREATMENT OF SCHIZOPHRENIA

BACKGROUND OF THE INVENTION

This invention relates to methods for treating schizophrenia and/or reducing the symptoms thereof.

Schizophrenia is a relatively intractable mental disorder. Although there can be, and often are, psycho-social aspects to the disease, it is well understood to have a clear physiological component. Many medical and psychopharmaceutical treatments have been used in this disorder, with varying degrees of success. However, as yet, there is no true understanding of the cause of the underlying biochemical nature of the disorder, nor any satisfactory long term treatment for it.

The manifestations of schizophrenia are numerous and often contradictory. The symptoms can be generally grouped into three groups; positive, or expressive symptomatology; negative, or deficit, symptomatology; and social symptomatology. Many schizophrenic patients are partially or completely refractory to standard anti-psychotic drug treatments. Currently, there are no adequate treatments for some symptoms of the disorder, especially negative symptoms which include amotivation, anhedonia, alogia, anergia, and affective impairment. These symptoms have profound effects on psychosocial function and rehabilitation potential.

Standard antipsychotic treatments in use today include the use of neuroleptics, which include such drugs as haloperidol and chlorpromazine. These medications generally act through blocking the dopamine $D_2$ receptor. In particular, these medications are thought to work through the selective reduction of dopaminergic tone in one or more of the four major brain dopamine tracts, i.e., the mesolimbic, the mesofrontal, the nigrostriatial and the tuberofundibular tracts. The mesolimbic tract is thought to be involved in the positive symptoms of schizophrenia; thus, reduction by antipsychotic medications of dopamine tone in this tract is thought to be involved in the therapeutic mechanism of those agents.

However, recent work by Weinberger (Arch. Gen. Psychiatry, XX, 1987) and others suggests that mesofrontal dopamine deficits may be implicated in negative schizophrenic symptoms. Consistent with this, most schizophrenics experience minimal negative symptom improvement or even worsening with standard neuroleptic treatment. Hence, the complex pathophysiology of schizophrenia includes both increased dopamine tone (in mesolimbic dopamine tracts) and decreased dopamine tone (in mesofrontal dopamine tracts). The treatment of schizophrenia with standard neuroleptics results in global reductions of dopamine neuron function in all dopamine tracts and thus may be responsible for the ineffective or deleterious responses of negative schizophrenic symptoms to neuroleptics.

Mazindol (5-hydroxy-5-p-chlorophenyl-2,3-dihydro-5H-imidazo[2,1-a]isoindole) is a long-acting agent that blocks dopamine reuptake at the dopamine transporter site located on the presynaptic neuron, and is in widespread clinical use as an anorectic. Its minimal side effects include restlessness and insomnia. Because of its cocaine-like dopamine reuptake inhibition, it is of use in both Parkinson's disease and narcolepsy. Although Parkinson's patients are notoriously sensitive to side effects, mazindol is a remarkably well tolerated drug. Out of twelve patients in a recent pilot study of mazindol for Parkinsonism, only two reported even mild side effects. (Delwaid, P. J., et al., "Mazindol in the treatment of Parkinson's disease," Arch Neurol. 40, 788-790, 1983.) In a recent report, unexpectedly, when given blindly to drug abusers, the oral clinical dose of mazindol was mildly dysphoric and free of abuse potential (Chait, et al., "Reinforcing and Subjective Effects of Several Anorectics in Normal Human Volunteers," J. Pharmaceutical Exp. Ther. 242, 777-83, 1987). However, prior to the present invention, mazindol was tested in schizophrenics (Krumholz, W.V. et al., "Clinical evaluation of mazindol in chronic schizophrenics," Curr. Therapeutic Res. 12, 609-610, 1970), and found to lead to an increase in schizophrenic symptomatology, to cause at the high doses which were administered enhancement of peripheral sympathetic activity, and therefore, not to be indicated in the treatment of chronic schizophrenia.

SUMMARY OF THE INVENTION

It has now been discovered that dopamine and noradrenergic reuptake inhibitors (e.g., that bind in a live human brain to a dopamine reuptake protein) and which are preferably not reinforcing after administration, are useful in treating negative symptoms in schizophrenics.

Thus, this invention relates to a method of treating negative symptoms in a schizophrenic patient, comprising administering to the patient an amount of a dopamine reuptake inhibitor effective to ameliorate said negative symptoms in the patient; and a method of treating negative symptoms in a schizophrenic patient, comprising administering to the patient an amount of a dopamine reuptake inhibitor effective to ameliorate said negative symptoms in the patient, further comprising administering to the patient an amount of an antipsychotic medication effective to ameliorate positive symptoms in the patient.

In a preferred embodiment, the dopamine or noradrenergic reuptake inhibitors of this invention function by binding to receptors on the dopamine reuptake protein. In a particularly preferred embodiment, the dopamine reuptake inhibitor is mazindol. In a preferred embodiment comprising coadministering antipsychotic medication, said medication is a neuroleptic, preferably haloperidol or chlorpromazine.

In another embodiment, the invention comprises a pharmaceutical composition comprising effective amounts of a dopamine or noradrenergic reuptake inhibitor and an antipsychotic medication and a pharmacologically acceptable excipient.

In view of the postulated mechanism of action of neuroleptic medications on dopamine tone in the various brain dopamine tracts discussed above, the possibility that pharmacological agents that enhance dopamine function could be useful in the treatment of negative symptoms in schizophrenia was considered. However, clearly, this would entail a risk of increasing positive symptoms in the attempt to ameliorate negative symptoms.

Mazindol increases synaptic dopamine in all dopamine tracts by blocking the reuptake of dopamine by the presynaptic dopamine reuptake site. The presence of inhibitory autoreceptors located on the presynaptic neuron serves to modulate excess dopamine stimulation in mesolimbic dopamine tracts, i.e., the increased presence of dopamine in the synapse will feed back on the presynaptic neuron via the autoreceptor to decrease neuron firing rates and slow down presynaptic dopamine release. In contrast, mesofrontal dopamine tracts lack these inhibitory autoreceptors; thus, enhanced dopaminergic tone, theoretically useful for treating negative symptoms, would be maintained in this area. Therefore, without wishing to be bound by theory, it was postulated that dopamine (and/or noradrenergic) reuptake inhibitors could be useful for treatment of negative symptoms in schizophrenia, if a useful "therapeutic window" could be defined that provides a balance between amelioration of negative symptoms and increasing of positive symptoms.

Mazindol is a complex pharmaceutical agent. In addition to its dopaminergic effects, mazindol also has properties of reuptake inhibition at noradrenergic and, to a lesser extent, serotonergic neurons. Again, without wishing to be bound by theory, while it is likely that mazindol's dopaminergic effects are the primary ones in the present invention, the drug's high noradrenergic binding may be involved in the mechanism of the drug's efficacy.

Suitable dopaminergic and/or noradrenergic reuptake inhibitors include those which increase the dopamine levels in the synapse, and thus are indirect dopamine agonists, and which have limited side effects at dosages effective for treating negative symptoms of schizophrenia. Generally, agents which increase dopamine levels in the synapse include such compounds as amphetamines, methylphenidate and ephedrine. However, amphetamines have serious side effects in that they are reinforcing (addictive) and long-term studies have shown that amphetamine use is related to the development of paranoid psychoses similar to schizophrenia; methylphenidate, which has a potent dopamine releasing effect, has been shown to exacerbate positive symptoms in schizophrenia; and ephedrine has excessive noradrenergic and antihistaminic side effects which are unacceptable. In particular, dopamine or noradrenergic reuptake inhibitors which are long-acting (i.e., which have high receptor affinity and slow receptor offrates) are preferred, as they avoid the side effects noted with amphetamine and cocaine. Mazindol is one of the reuptake inhibitors which has these properties.

Like amantadine, mazindol is an indirect dopamine agonist. Preclinically, it shares more properties in common with cocaine than does amantadine. Specifically, mazindol is a dopaminergic, noradrenergic and serotonergic reuptake inhibitor like cocaine, and it induces the same behavioral stereotypes and conditioned place preference as cocaine, and even substitutes for cocaine in self-administration studies in animals. Most notably in the striatum of the brain a common receptor on the dopamine reuptake carrier has been proposed for both mazindol and cocaine, and the investigators propose that this receptor may mediate cocaine's reinforcing and abuse potential in man. (Ritz, et al., "Cocaine receptors on dopamine transporters are related to cocaine self-administration," Science 1219–1223, 1987.)

In this application, the term "schizophrenia" has its conventional meaning, e.g., the constellation of symptoms described in the DSM-III-R. Negative symptoms of schizophrenia are conventionally understood to be a subset of these symptoms, and are described in various references, e.g., in Andreasen, N. C., Arch. Gen. Psychiatry 39, 784 (1982).

By "ameliorating" is meant lessening or making more normal the abnormal symptoms suffered by a patient prior to treatment to an extent considered by the clinician to be therapeutically significant. There are various tests known in the art for measuring such symptoms, e.g., the Brief Psychiatric Rating Scale (BPRS) and the Positive and Negative Symptom Scale (PANSS). Amelioration of symptoms generally is considered significant if these ratings improve 10% or more, preferably 25% or more.

The term "reinforcing," as used herein, has its standard meaning, e.g., and refers to, e.g., effects of a substance which cause self-administration thereof in animals or which support animal behavioral patterns paired with the substance or which cause a substance to be rated by addicts as possessing reinforcing characteristics in standard tests. The substances used in this invention are preferably non-reinforcing and therefore non-addictive. It is important to note that a substance can be reinforcing by one route of administration (e.g., injection) and not by another (e.g., orally). Thus, the term "reinforcing" refers to the results which occur by the route of administration used for the anti-negative symptom or other treatment of this invention. The lack of reinforcement can be conventionally determined using routine procedures.

The agents useful in the methods of this invention are those which are dopamine reuptake inhibitors, which bind to the receptor for the substance in a live brain and which have few or insignificant side effects, e.g., they are not reinforcing by the chosen route of administration, do not aggravate positive symptoms, have therapeutically acceptable noradrenergic and antihistaminic side effects, etc. Agents which are dopamine reuptake inhibitors binding to the reuptake protein for dopamine are known and/or can be chosen by standard pharmacological in vitro protocols, e.g., using brain samples, e.g., as disclosed in Janowsky et al., J. Neurochem., Vol. 46, pp. 1272–1276 (1986). Routine clinical tests can thereafter be utilized to determine the clinical efficacy of a thus-chosen candidate agent.

Typically, effective dosages will be those amounts for which a candidate agent is effective for other uses of the agent, if any. Thus, mazindol can be utilized in dosages for which it is approved for administration for other purposes, such as anorectic treatment. The same is true for the GBR compounds (useful as antidepressants). For mazindol, see, e.g., the Physicians Desk Reference, where suitable dosages are given. For an individual case, the usual considerations prevalent in the pharmaceutical industry will be employed to determine preferred precise dosages, including the state of health of the patient, the age, the body weight, the activity of the agent as indicated by the protocols mentioned above, and data gathered in preliminary clinical tests, etc. All modes of administration are applicable, including oral, injection, transdermal, etc.

In particular, it is noted that one aspect of this invention comprises the recognition that there is a rather narrow "therapeutic window" for the dopamine and/or noradrenergic reuptake inhibitors in conjunction with specifically negative symptoms which was not previously appreciated by investigators skilled in the art. Thus, as was discussed previously, mazindol had previously been investigated as an antischizophrenic agent, but it was administered to a population not selected for having primarily negative symptoms susceptible to treatment with dopamine reuptake inhibitors, and furthermore, the mazindol was administered at dosages now found to be far in excess of the ranges found to be effective for use in treatment of negative symptoms.

For the treatment of negative symptoms in schizophrenic patients, administration of dopamine or noradrenergic reuptake inhibitors may be performed before, during, after and/or between administration of other antipsychotic medication, e.g., neuroleptics. In particular, the inhibitors are useful for amelioration of the negative symptoms induced by the standard neuroleptic therapy. Thus, the methods of this invention can be of both a prophylactic and therapeutic nature.

Suitable dopaminergic and/or noradrenergic reuptake inhibitor agents for use in the methods of this invention which satisfy the functional criteria of being reuptake inhibitors which bind in a live brain (e.g., human) to a dopamine and/or noradrenergic reuptake protein and which alleviate negative schizophrenic symptoms in the particular mode of administration without inducing excessive side effects include mazindol, GBR compounds (which are well known in the antidepressant field, for example), benztropine, buproprion, etc. Also useful are the compounds disclosed in Bogeso et al., J. Med. Chem., Vol. 28, p. 1817 (1985), e.g., Lu 19-005 (+)trans-3(3,4-dichloro-phenyl)-N-methyl-1-indanamine. As was mentioned above, methylphenidate (ritalin) is not generally useful in this invention because it has a potent dopamine releasing effect and has been shown to increase positive symptoms in schizophrenia. Furthermore, methylphenidate is a reinforcing dopamine reuptake inhibitor. Similarly, pemoline may be useful in this invention, but has been reported to cause psychotic symptoms in adults after chronic ingestion and may have abuse potential.

GBR compounds include 1-[2-(diphenylmethoxy)-ethyl]piperazines, optionally substituted, especially those wherein the piperazine is 4-substituted by, e.g., 4-(3-phenyl-2-prop(en)yl), and those wherein the diphenylmethoxy group is substituted by one or more strongly inductive groups having small volume analogous to those of van der Zee et al., Eur. J. Med. Chem. Chemica Therapeutica, July–August 1980-15, No. 4, pp. 363-370, e.g., selected from those discussed in standard texts of organic chemistry, e.g., Morrison & Boyd, (*Organic Chemistry*, 4th Ed., New York Univ., 1983), and/or those wherein the solitary phenyl group on the 4-piperazine substituent is substituted by one or more substituents having a strong electron withdrawing effect and a small volume as defined above and, e.g., selected from those discussed in standard texts of organic chemistry, e.g., Morrison et al. A preferred agent is GBR 12921 (1-[2-(diphenylmethoxy)-ethyl]-4-(3-phenyl-2-propenyl)piperazine hydrochloride).

Suitable antipsychotic agents for use in the methods of this invention include those which are known in the art for the treatment of schizophrenia, particularly those which satisfy the functional criteria disclosed in, e.g., The Practitioner's Guide to Psychoactive Drugs, 3rd Ed., Bassuk, E., et al., eds., Plenum Medical Books, New York (1991). Haloperidol and chlorpromazine are examples of such neuroleptics.

All routes of administration are applicable for this invention. However, oral administration is preferred.

Typical administration regimens for a given class of patients can involve various combinations of timing of administration as can be routinely determinable using conventional considerations. Thus, it is possible to administer one dose of a suitable agent at the same time every day and in addition have the patient self-administer additional doses during negative symptom episodes during that day up to a maximum number of doses conventionally determinable.

For a given patient, administration will generally continue until the number or severity of negative symptom episodes diminishes to a point where dosage of the agent can be decreased to a maintenance level according to the methods of this invention.

In general, dopamine reuptake inhibitors will be used alone (not in conjunction with other antipsychotics) when negative symptoms are the primary diagnosis.

In patients requiring both antipsychotic medication as well as dopamine or noradrenergic reuptake inhibitors, the reuptake inhibitors can be administered simultaneously with, before or after the antipsychotics. In a preferred embodiment, antipsychotic agents can be combined with reuptake inhibitors to provide a combination product having improved properties for the treatment of schizophrenia. These combination pharmaceutical preparations contain conventional amounts of both the antipsychotic as well as the reuptake inhibitor, which are either known or can be conventionally determined, as noted above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, are hereby incorporated by reference.

EXAMPLES

Example 1

The response of positive and negative symptoms to mazindol augmentation of neuroleptic medication was studied in partially refractory, stable outpatient schizophrenics.

In this study, outpatients stabilized on neuroleptic medication were enrolled in a double-blind, placebo controlled trial of mazindol (2 mg/day) augmentation of typical neuroleptic agents, e.g., fluphenazine, thioridazine, haloperidol, etc. BPRS and PANSS ratings of negative symptoms, as well as abnormal involuntary movement scale (AIMS: a scale for measuring tardive dyskinesia, a motor side effect of neuroleptics), Webster extrapyramidal side effects (EPS: a scale for measuring neuroleptic side effects) ratings and fasting prolactin and homovanillic acid (HVA: a metabolite of dopamine that provides a rough measure of brain dopamine turnover) levels were obtained for four weeks prior to mazindol/placebo augmentation and for six to eight weeks after randomization.

Nine patients receiving active mazindol demonstrated a 30–40% reduction of BPRS and PANSS negative symptom ratings compared to placebo mazindol patients (n=8). Increases in positive symptoms were noted in one patient who received a pilot dose of 8 mg/day of mazindol. No other increases in positive symptoms were seen in patients treated with 2 mg/day of mazindol. There was a modest reduction of extrapyramidal side effects and 1/9 patients showed a worsening of tardive dyskinesia with mazindol. Subjectively, 7/9 patients experienced increased mood, energy, and affective reactivity and correctly guessed the identity of the randomized medication.

Example 2

In another ongoing study, patients who participated in a placebo-controlled trial of mazindol augmentation of typical antipsychotic medications received open-label mazindol (2–4 mg/day) in addition to typical neuroleptics. BPRS, PANSS, AIMS, Webster's EPS ratings, and fasting prolactin and HVA were obtained biweekly for 4–6 months of mazindol treatment.

Patients receiving mazindol demonstrated a 25–30% reduction of BPRS and PANSS negative symptom ratings compared to their baseline. No increases in positive symptoms were noted in any patients. There was a modest reduction of extrapyramidal side effects with mazindol. Subjectively, patients experienced increased mood, energy, and affective reactivity and requested to be maintained on the medication. No patients developed tolerance to the beneficial effects of mazindol.

Thus, these data indicate that mazindol is effective for treatment of refractory negative symptoms in otherwise stable outpatient schizophrenics. There was no worsening of positive psychotic symptoms and minimal effects on tardive dyskinesia with mazindol treatment. Most patients experienced fewer extrapyramidal side effects after mazindol augmentation. The data further support the conclusion that mazindol is a useful adjunct to standard neuroleptic medication for treatment of refractory negative symptoms in otherwise stable outpatient schizophrenics.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating negative symptoms in a schizophrenic patient, comprising administering to the patient an amount of a non-reinforcing dopamine or noradrenergic reuptake inhibitor, or both, effective to ameliorate said negative symptoms in the patient.

2. A method of claim 1, wherein the dopamine reuptake inhibitor is mazindol.

3. A method of claim 1, further comprising administering to the patient an amount of an antipsychotic medication effective to ameliorate positive symptoms in the patient.

4. A method of claim 3, wherein the antipsychotic medication is a neuroleptic.

5. A method of claim 4, wherein the neuroleptic is haloperidol.

6. A method of claim 2, further comprising administering to the patient an amount of an antipsychotic medication effective to ameliorate positive symptoms in the patient.

7. A method of claim 6, wherein the antipsychotic is a neuroleptic.

8. A method of claim 7, wherein the neuroleptic is haloperidol.

9. A method of claim 1, wherein said non-reinforcing dopamine reuptake inhibitor is a GBR compound, benztropine, buproprion or mazindol.

10. A method of claim 1, wherein said administering is effected during an episode of negative symptoms.

11. A method of claim 1, wherein said administering is effected prophylactically.

12. A method of claim 1, wherein said dopamine reuptake inhibitor binds to the dopamine reuptake protein.

13. A pharmaceutical preparation comprising effective amounts of a dopamine reuptake inhibitor and an antipsychotic, and a pharmaceutically acceptable excipient.

* * * * *